(12) United States Patent
Van Beuningen et al.

(10) Patent No.: US 7,364,848 B2
(45) Date of Patent: Apr. 29, 2008

(54) INTEGRATED MICROARRAY ANALYSIS

(75) Inventors: Marinus Gerardus Johannes Van Beuningen, Oss (NL); Tim Kievits, Vught (NL)

(73) Assignee: PamGene B.V., Den Bosch (NL)

( * ) Notice: Subject to any disclaimer, the term of this patent is extended or adjusted under 35 U.S.C. 154(b) by 370 days.

(21) Appl. No.: 10/526,261

(22) PCT Filed: Sep. 1, 2003

(86) PCT No.: PCT/EP03/09980

§ 371 (c)(1),
(2), (4) Date: Mar. 1, 2005

(87) PCT Pub. No.: WO2004/020667

PCT Pub. Date: Mar. 11, 2004

(65) Prior Publication Data

US 2006/0035231 A1    Feb. 16, 2006

Related U.S. Application Data

(60) Provisional application No. 60/421,468, filed on Oct. 25, 2002.

(30) Foreign Application Priority Data

Sep. 2, 2002   (EP)   .................... 02447163

(51) Int. Cl.
*C12Q 1/68* (2006.01)
*C12N 15/11* (2006.01)
*C12N 9/12* (2006.01)
*C12N 9/14* (2006.01)

(52) U.S. Cl. .................. 435/6; 536/23.1; 435/194; 435/195

(58) Field of Classification Search .................. None
See application file for complete search history.

(56) References Cited

U.S. PATENT DOCUMENTS 5,691,146 A    11/1997   Mayrand
2004/0048270 A1    3/2004   Zeltz et al.

FOREIGN PATENT DOCUMENTS

| EP | 0 745 690 A2 | 12/1996 |
| WO | WO 99/02266 | 1/1999 |
| WO | WO 00/31304 | 6/2000 |
| WO | WO 01/19517 A1 | 3/2001 |
| WO | WO 01/31063 A1 | 5/2001 |
| WO | WO 01/34842 A2 | 5/2001 |
| WO | WO 01/48242 A2 | 7/2001 |

OTHER PUBLICATIONS

Belgrader et al., "Rapid Pathogen Detection Using a Microchip PCR Array Instrument." Clinical Chemistry 44, 10:2191-2194 (1998).
Strizhkov et al., "PCR Amplification on a Microarray of Gel-Immobilized Oligonucleotides: Detection of Bacterial Toxin- and Drug-Resistant Genes and Their Mutations." BioTechniques 29:844-857 (Oct. 2000).
Huber et al., "Accessing Single Nucleotide Polymorphisms in Genomic DNA by Direct: Multiplex Polymerase Chain Reaction Amplification on Oligonucleotide Microarrays." Analytical Biochemistry 303:25-33 (2002).
Carmon et al., "Solid-Phase PCR in Microwells: Effects of Linker Length and Composition on Tethering, Hybridization, and Extension." BioTechniques 32:410-420 (Feb. 2002).
van Beuningen et al., "Fast and Specific Hybridization Using Flow-Through Microarrays on Porous Metal Oxide." Clinical Chemistry 47:1931-1933 (2001).
Ortiz et al., "PNA Molecular Beacons for Rapid Detection of PCR Amplicons." Molecular and Cellular Probes 12:219-226 (1998).

*Primary Examiner*—James Martinell
(74) *Attorney, Agent, or Firm*—Amster, Rothstein and Ebenstein LLP

(57) ABSTRACT

The present invention relates to methods for identifying analyte nucleic acids present in a sample comprising nucleic acid molecules, said method comprising the steps of: (a) providing a porous substrate, said substrate comprising a plurality of micro-channels, wherein said micro-channels have immobilized thereon a target molecule capable of binding to an analyte present in said sample; wherein said channels are further provided with analyte amplification components, a reporter system; and said sample; (b) amplifying analyte nucleic acid molecules present within said sample; and (c) allowing binding to take place between an amplified analyte nucleic acid obtained in step (b), said target molecule immobilized onto the channels of said substrate and said reporter system, wherein said reporter system allows detecting whether binding has occurred between said target molecule and said analyte nucleic acid. The present invention further relates to the use of said methods as well as kits for carrying out said methods.

20 Claims, No Drawings

INTEGRATED MICROARRAY ANALYSIS

This application is a U.S. National Phase of PCT Application Ser. No. PCT/EP2003/009980, filed Sep. 1, 2003 and claims priority to European Application No. 02447163.3, filed Sep. 2, 2002 and U.S. Provisional Application No. 60/421,468, filed Oct. 25, 2002.

FIELD OF THE INVENTION

The present invention relates to methods useful in the detection and quantification of an analyte(s) in a sample including integrated amplification, identification and analysis steps. More particularly, this invention relates to matter for performing active, multi-step nucleic acid sequence amplification and diagnostic analyses.

The methods of the invention are useful in a variety of applications, including, for example, disease diagnostics (infectious and otherwise), genetic analyses, agricultural and environmental applications, drug discovery, pharmacogenomics, and food and/or water monitoring and analysis.

BACKGROUND

The detection of specific nucleic acids is an important tool for diagnostic medicine and molecular biology research. Gene probe assays currently play roles in identifying infectious organisms such as bacteria and viruses, in probing the expression of normal genes and identifying mutant genes such as oncogenes, in typing tissue for compatibility preceding tissue transplantation, in matching tissue or blood samples for forensic medicine, and for exploring homology among genes from different species.

Ideally, a gene probe assay should be sensitive, specific and be able to be easily automated. Sensitivity, i.e. detection limits, remains a significant obstacle in nucleic acid detection systems, in particular where only small-volume and/or low concentration samples are available. A variety of techniques have been developed to address this issue including analyte amplification. Analyte amplification involves the amplification (i.e. replication) of the analyte sequence being detected in a sample, resulting in a significant increase in the number of analyte molecules. The requirement for sensitivity (i.e. low detection limits) has been greatly alleviated by the development of the polymerase chain reaction (PCR) and other amplification technologies, which allow researchers to amplify exponentially a specific nucleic acid sequence before analysis.

In their standard format, amplification technologies for nucleic acid analysis have a number of limitations to their commercial utilization including the cost of the reagents and the ability to automate the process.

In microarray technology, varied and important information is generated and many potential applications are provided. The use of these microarrays in research, diagnostic and related applications has grown considerably and is expected to continue to do so. A variety of different array technologies have been developed in order to meet the growing need of the biotechnology industry, as evidenced by the extensive number of patents and other literature published.

In view of the micro formats of the samples that are used for microarray analysis, amplification of the analyte molecules is certainly desired. The feasibility of miniaturized amplification reactions was demonstrated in US 2002/0037510 A1 wherein amplification reactions performed within micro spots arrayed on a glass slide are disclosed.

However, as well appreciated in the art, there is a continuous and expanding need for improved microarray analysis methods securing rapid, highly specific methods of identifying and quantifying chemical, biochemical and biological substances as analytes in research and diagnostic mixtures.

It is an object of the present invention to provide improved detection limits and time management practices in automated microarray analysis systems. It is an object of the present invention to provide high-throughput microarray analysis methods with integrated amplification-hybridization-detection of sample analytes. As such, in addition to large scale miniaturized sensitive analysis practices, the present invention provides a parallel amplification/identification of analyte molecules in a sample, thereby further integrating an efficient direct detection of the identified amplified sample analytes. Any time-consuming step of e.g. a pre-analysis amplification step and/or washing off excess label for detection is omitted.

SUMMARY OF THE INVENTION

The present invention provides a method for identifying an analyte nucleic acid in a sample comprising the steps of:
(a) providing a porous substrate, said substrate comprising a plurality of micro-channels, wherein said micro-channels have immobilized thereon a target molecule capable of binding to an analyte present in said sample; wherein said channels are further provided with analyte amplification components,
a reporter system; and
said sample;
(b) amplifying analyte nucleic acid molecules present within said sample; and
(c) allowing binding to take place between an amplified analyte nucleic acid obtained in step (b), said target molecule immobilized onto the channels of said substrate and said reporter system, wherein said reporter system allows detecting whether binding has occurred between said target molecule and said analyte nucleic acid.

The main advantage of the present invention is based on the integration of the binding of produced reaction components or amplicons to the target molecules immobilized on the surface of the channels or pores localized within the porous substrate and the actual reaction within said channels or pores.

The present invention further allows an integrated labelling step and as such allows for a high-throughput automated system.

Additional features and advantages of the invention will be set forth in the detailed description which follows, and in part will be apparent from the description, or may be learned by practice of the invention. The objectives and other advantages of the invention will be realized and attained by the process particularly pointed out in the written description and appended claims.

DETAILED DESCRIPTION OF THE INVENTION

The present invention relates in particular to integrated amplification-hybridization-detection assays of analyte nucleic acids within a sample.

Before the present method and solutions used in the method are described, it is to be understood that this invention is not limited to particular methods, components, or solutions described, as such methods, components, and solutions may, of course, vary.

In the present specification and the appended claims, the singular forms "a", "an", and "the" include plural references unless the context clearly dictates otherwise.

It should also be understood that the terminology used herein is not intended to be limiting, since the scope of the present invention will be limited only by the appended claims.

Accordingly, definitions should not be understood to limit the scope of the invention. Rather, they should be used to interpret the language of the description and, where appropriate, the language of the claims. These terms may also be understood more fully in the context of the description of the invention. If a term is included in the description or the claims that is not further defined within the present description, or that cannot be interpreted based on its context, then it should be construed to have the same meaning as it is understood by those skilled in the art.

Although any methods and materials similar or equivalent to those described herein may be used in the practice or testing of the present invention, the preferred methods and materials are described herein.

A number of materials suitable for use as substrates in the present invention have been described in the art. Materials particularly suitable for use as substrates in the present invention include any type of porous substrates known in the art. More materials particularly suitable for use as substrates in the present invention include any type of solid porous substrates known in the art. The term "porous substrate" as used in the present specification refers to a substrate possessing or full of pores, wherein the term "pore" refers to a minute opening or microchannel by which matter may be either absorbed or passed through. Particularly, where the pores allow passing-through of matter, the substrate is likely to be permeable.

The substrate may be in the form of beads, particles, sheets, films or membranes and may be permeable. For example, the substrate may consist of fibres (such as glass wool or other glass or plastic fibres), glass or plastic capillary tubes, or metal oxide membranes. The porous substrate may be planar or have simple or complex shape. The surface to which the molecule is adhered may be an external surface or an internal surface of the porous substrate. Particularly where the surface is porous, the molecule is likely to be attached to an internal surface. Where the solid surface is porous, various pore sizes may be employed depending upon the nature of the system.

The material of the porous substrate may be, for example, a metal, a ceramic metal oxide or an organic polymer. As a metal, for example, a porous substrate of stainless steel (sintered metal) may be used. For applications not requiring heat resistance, a porous substrate of an organic polymer may also be used if it is sufficiently rigid. Above all, in view of heat resistance and chemical resistance, a metal oxide may be used. In addition, metal oxides provide a substrate having both a high channel density and a high porosity, allowing high density arrays comprising different target molecules per unit of the surface for sample application. In addition, metal oxides are highly transparent for visible light. Metal oxides are relatively cheap substrates that do not require the use of any typical microfabrication technology and, that offer an improved control over the liquid distribution over the surface of the substrate, such as electrochemically manufactured metal oxide membrane. Metal oxide membranes having through-going, oriented channels may be manufactured through electrochemical etching of a metal sheet.

Accordingly, in one embodiment of the present invention, a method is provided as described herein, wherein said porous substrate is a metal oxide substrate.

The kind of metal oxide is not especially limited. Metal oxides considered are, among others, oxides of zirconium, silicium, mullite, cordierite, titanium, zeolite or zeolite analog, tantalum, and aluminium, as well as alloys of two or more metal oxides and doped metal oxides and alloys containing metal oxides.

In one embodiment, a method as described herein is provided, wherein said porous substrate is an aluminium oxide substrate.

Metal oxide substrates or membranes as employed in the methods of the present invention may be anodic oxide films. As well known in the art, an aluminium metal substrate may be anodized in an electrolyte to produce an anodic oxide film. The anodization process results in a system of larger pores extending from one face and interconnects with a system of smaller pores extending in from the other face. Pore size is determined by the minimum diameters of the smaller pores, while flow rates are determined largely by the length of the smaller pores, which can be made very short. Accordingly, such membranes may have oriented through-going partially branched channels with well-controlled diameter and useful chemical surface properties. Useful thicknesses of the metal oxide substrates or membranes as employed in the methods of the present invention may for instance range from 50 µm to 150 µm (including thicknesses of 60, 70, 80, 90, 100, 110, 120, 130 and 140 µm). A particular suitable example of substrate thickness is 60 µm.

A suitable substrate pore diameter ranges from 150 to 250 nm including 160, 170, 180, 190, 200, 210, 220, 230 and 240 nm. A particular suitable example of pore diameter is 200 nm. These dimensions are not to be construed as limiting the present invention.

Advantageously, such membranes are transparent, especially if wet, which allows for assays using various optical techniques. WO 99/02266 which discloses the Anopore™ porous substrate is exemplary in this respect, and is specifically incorporated by reference in the present invention.

Particular useful porous substrates as employed in the methods described in the present specification are 3-dimensional substrates, which allow pressurized movement of fluid, e.g. the sample solution, through its structure. As such, particular useful porous substrates as employed in the present methods possess a permeable or flow-through nature. In contrast with two-dimensional substrates, 3-dimensional substrates or microarrays as employed in the methods as described herein give significantly reduced hybridization times and increased signal and signal-to-noise ratios. Further, a positive or negative pressure may be applied to the arrays in order to pump the sample solution dynamically up and down through the substrate pores. Said dynamical pumping allows immediate removal and ability to perform real-time detection of generated products from a reaction which takes place within the pores of the substrate by fast binding of said generated products to the substrate pore walls.

In a further embodiment, a method as described herein is provided wherein said porous substrate is a flow-through substrate.

The nature and geometry of the porous substrate to be used in the present invention will depend upon a variety of factors, including, among others, the type of array (e.g., one-dimensional, two-dimensional or three-dimensional) and the mode of attachment (e.g., covalent or non-covalent). Generally, the substrate according to the present invention may be composed of any porous material which will permit immobilization of a target-molecule and which will not melt or otherwise substantially degrade under the reaction conditions used.

The expression "immobilized on a porous substrate" as used in the present specification refers to the attachment or adherence of one or more target-molecules to the surface of a porous substrate including attachment or adherence to the inner surface of said substrate.

Molecules or compounds may be immobilized either covalently (e.g., utilizing single reactive thiol groups of cysteine residues,) or non-covalently but specifically (e.g., via immobilized antibodies, the biotin/streptavidin system, and the like), by any method known in the art. Where covalent immobilization is contemplated, the substrate should be polyfunctional or be capable of being polyfunctionalized or activated with reactive groups capable of forming a covalent bond with the target to be immobilized (e.g. carboxylic acids, aldehydes, amino groups, cyano groups, ethylenic groups, hydroxyl groups, mercapto groups and the like).

Further examples of the various methods that are available to attach target-molecules to porous substrates include but are not limited to biotin-ligand non-covalently complexed with streptavidin, SH-ligand covalently linked via an alkylating reagent such as an iodoacetamide or maleimide which reacts with SH and forms a thioether bond, amine-ligand covalently linked via an activated carboxylate group (e.g., EDAC coupled, etc.), phenylboronic acid (PBA)-ligand complexed with salicylhydroxamic acid (SHA), and acrylic linkages allowing polymerization with free acrylic acid monomers to form polyacrylamide or reaction with SH or silane surfaces. More specifically, immobilization of proteins may be accomplished through attachment agents selected from the group comprising cyanogen bromide, succinimides, aldehydes, tosyl chloride, avidin-biotin, photo-crosslinkable agents including hetero bifunctional cross-linking agents such as N-γ-maleimidobutyryloxylsuccinimide ester (GMBS), epoxides, and maleimides. Antibodies may be attached to a porous substrate by chemically cross-linking a free amino group on the antibody to reactive side groups present within the support. For example, antibodies may be chemically cross-linked to a substrate that contains free amino, carboxyl, or sulfur groups using glutaraldehyde, carbo-di-imides, or hetero bi-functional agents such as GIVMS as cross-linkers.

So-called linker molecules may be useful in the application for spacing the target-molecules away from the activated substrate. Linkers may be long or short, flexible, semi-rigid or rigid, charged or uncharged, hydrophobic or hydrophilic, depending on the particular application. Particular useful linkers which may be present on the surface of a substrate and used for attachment of target molecules to said surface are bifunctional, i.e. they will have one functional group or moiety capable of forming a linkage with the activated substrate and any other functional group or moiety capable of forming a linkage with another linker molecule or the target-molecule.

In certain circumstances, linkers may be used to "convert" one functional group into another. For example, an amino-activated substrate can be converted into a hydroxyl-activated substrate by reaction with, for example, 3-hydroxy-propionic acid. In this way, substrate materials which cannot be readily activated with a specified reactive functional group can be conveniently converted into an appropriately activated substrate. Chemistries and reagents suitable for "converting" such reactive groups are well known, and will be apparent to those skilled in the art.

Linkers may also be used, where necessary, to increase or "amplify" the number of reactive groups on the activated substrate. For this embodiment, the linker will have three or more functional groups. Following attachment to the activated substrate by way of one of the functional groups, the remaining two or more groups are available for attachment of target molecules such as oligonucleotides and polynucleotides. Amplifying the number of functional groups on the activated substrate in this manner is particularly convenient when the substrate cannot be readily activated with a sufficient number of reactive groups.

Suitable linkers or cross-linker molecules include, by way of example and not limitation, polypeptides such as polyproline or polyalanine, saturated or unsaturated bi-functional hydrocarbons such as 1-amino-hexanoic acid, polymers such as polyethylene glycol, etc., 1,4-Dimethoxytrityl-polyethylene glycol phosphoramidites useful for forming phosphodiester linkages with hydroxyl groups and are described, for example in Zhang et al., 1991, Nucl. 20 Acids Res. 19:3929-3933 and Durand et al., 1990, Nucl. Acids Res. 18:6353-6359. Other useful linkers are commercially available.

It is contemplated that in general the target molecule is covalently bound to the substrate. This minimizes loss of said molecule from the substrate. Covalent binding of an organic compound to a metal oxide is well known in the art, for example using the method described by Chu. C. W. et al. (J. Adhesion Sci. Technol., 7, pp. 417-433, 1993) and Fadda, M. B. et al. (Biotechnology and Applied Biochemistry, 16, pp. 221-227, 1992). Further, after activation of a metal oxide support by a silanating agent and binding of the biomolecules, a number of amino-groups of said silanating agent can still be present as unloaded amino-groups. This may result in unwanted interactions of said amino-groups with various substances present in the medium in which the loaded support is used, resulting in high background signals. The unloaded amino-groups can be removed from the support without affecting the loaded part of the support by subsequently treating the loaded support with an acidic solution. Similarly, an activated and loaded support may be treated with a basic or neutral solution, provided that the method is not used for derivatization of aluminiumoxide nanoparticles aminated with (3-aminopropyl)-triethoxysilane, wherein the basic solution further contains a large excess of N-acetylhomocysteinelactone. In this regard, the application WO 01/12846 is exemplary, and is specifically incorporated in the present invention.

The terms "target" and "target-molecule" are used interchangeably throughout the present invention and refer to molecules immobilized on a substrate; also referred to as immobilized probes or capture probes. A wide variety of different molecules can be immobilized on the substrate of the present arrays. Similarly, the present methods are applicable to a wide variety of different molecules or targets that may be immobilized on the substrate of the present arrays. A target or target-molecule as used in the present specification refers to any molecule which may be attached to a substrate for the purpose of performing microarray analysis for detection and identification of a particular analyte. A target further refers to a molecule that may be recognized by and/or interact with a particular amplified analyte.

The methods and arrays are particularly exemplified herein in terms of nucleic acid sequences including deoxyribonucleic acids (DNA, cDNA), ribonucleic acids (RNA, mRNA, cRNA, aRNA), peptide nucleic acids (PNA) and/or fragments thereof including polynucleotides and oligonucleotides as targets immobilized on a substrate.

The immobilized molecules may be tailored to specifically bind to or hybridize with specified analyte molecules. For example, if the array is used to determine expression of a particular gene from a cDNA library that has been reverse transcribed from mRNA molecules, the immobilized molecules will be constructed with a sequence complementary or otherwise capable of recognizing the gene, gene fragment or expression products of such gene or gene fragments. In this context, the nucleic acids may be derived from any biological sources including, but not limited to, human, animal, plants, bacterial, fungal, viral, environmental or other sources.

The composition of the immobilized target molecules, e.g., polynucleotides is not critical. The only requirement is that they be capable of hybridizing to an analyte molecule of complementary sequence, e.g. nucleic acids, if any. For example, immoblized polynucleotides may be composed of all natural or all synthetic nucleotide bases, or a combination of both. Non-limiting examples of modified bases suitable for use with the instant invention are described, for example, in Practical Handbook of Biochemistry and Molecular biology, G. Fasman, Ed., CRC Press, 1989, pp. 385-392. While in most instances polynucleotides will be composed entirely of the natural bases (A, C, G, T or U), in certain circumstances the use of synthetic bases may be preferred.

Moreover, while the backbones of immobilized polynucleotides will typically be composed entirely of "native" phosphodiester linkages, they may contain one or more modified linkages, such as one or more phosphorothioate, phosphoramidite or other modified linkages. As a specific example, one or more immobilized polynucleotides may be a peptide nucleic acid (PNA), which contains amide interlinkages. Additional examples of modified base and backbones that may be used in conjunction with the invention, as well as methods for their synthesis can be found, for example, in Uhlman & Peyman, 1990, Chemical Review 90(4): 544-584; Goodchild, 1990, Bioconjugate Chem. 1(3): 165-186; Egholm et al., 1992, J. Am. Chem. Soc. 114:1895-1897, as well as the references cited in all of the above. Modifications in the native structure, including alterations in the backbone, sugars or heterocyclic bases, have been shown to increase intracellular stability and binding affinity. Among useful changes in the backbone chemistry are phosphorothioates; phosphoro-dithioates, where both of the non-bridging oxygens are substituted with sulfur; phosphoroamidites; alkyl phosphotriesters and boranophosphates. A-chiral phosphate derivatives include 3'-O-5'-S-phosphorothioate, 3'-S-5'-O-phosphorothioate, 3'-$CH_2$-5'-O-phosphonate and 3'-NH-5'-O-phosphoroamidate. Peptide nucleic acids replace the entire ribose phosphodiester backbone with a peptide linkage. Locked nucleic acids give additional conformational stability of sugar moiety due to additional bonds between 2'-carboxyl and 5' carboxyl or 4'-carboxyl groups of deoxyribose. Sugar modifications are also used to enhance stability and affinity. The a-anomer of deoxyribose may be used, where the base is inverted with respect to the natural p-anomer. The 2'-OH of the ribose sugar may be altered to form 2'-O-methyl or 2'-O-allyl sugars, which provides resistance to degradation without comprising affinity. Modifications of the heterocyclic bases that find use in the method of the invention are those capable of appropriate base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

Examples of non-naturally occurring bases that are capable of forming base-pairing relationships include, but are not limited to, aza- and deaza-pyrimidine analogues, aza- and deaza-purine analogues, and other heterocyclic base analogues, wherein one or more of the carbon and nitrogen atoms of the purine and pyrimidine rings have been substituted by heteroatoms, e.g., oxygen, sulfur, selenium, phosphorus, and the like.

The length of the immobilized molecules, in instances where they are nucleotides, polynucleotides, nucleic acids or similar polymers, will usually range between 5 to 1000 nucleotides, optionally 5 to 500 nucleotides, further optionally 5 to 250 nucleotides, still further optionally, 5 to 75 nucleotides. The polynucleotide, oligonucleotide or nucleic acid probes may be double or single stranded, or PCR fragments amplified from cDNA.

Immobilized polynucleotides may make up a "universal set" for e.g. sequencing a nucleic acid, as discussed in WO 98/31836, particularly pages 27-29. Alternatively, the set of polynucleotides may correspond to particular mutations that are to be identified in a known sequence.

The methods and arrays according to the present specification are equally applicable to other types of molecules. For example, one skilled in the art could easily adapt the present methods and arrays to apply to targets including for example proteins such as transcription factors, drugs, toxins, liposomes and more.

In the present invention, a target-molecule is immobilized on the substrate at a spatially predefined region, i.e. at a particular spot. The terms "predefined region" or "spot" are used interchangeably in the present specification and relate to individually, spatially addressable positions on an array.

A predefined region is a localized area, typically on the top-surface of the substrate which is, was, or is intended to be used to target molecule deposition. Subsequent target molecule immobilization may be on said top surface (external) or on the surface of the pores within a porous substrate (internal surface) or both.

The microarrays of the present invention may be of any desired size, from two spots to $10^6$ spots or even more. The upper and lower limits on the size of the substrate are determined solely by the practical considerations of working with extremely small or large substrates.

For a given substrate size, the upper limit is determined only by the ability to create and detect spots on the microarray.

The preferred number of spots on a microarray generally depends on the particular use to which the microarray is to be put. It will be understood that the spot density as used herein relates to the number of spatially predefined regions per square millimetre as determined by the view on the planar, two-dimensional (2D) top surface of the substrate.

For example, sequencing by hybridization will generally require large arrays, while mutation detection may require only a small array. In general, microarrays according to the present invention contain from 2 to 10,000 spots per square millimetre planar surface. A particular useful spot density is within a range of 2 to 1000 spots per $mm^2$. A more particular useful spot density is within a range of 2 to 100 spots per $mm^2$. Usually a microarray useful in the present invention has a spot density of 25 spots per $mm^2$.

Furthermore, not all spots on the microarray need to be unique. Indeed, in many applications, redundancies in the spots are desirable for the purposes of acting as internal controls.

Methods and arrays of the present invention may have incorporated the use of immobilized internal references which may bind to reporter molecules to correct for signal errors due to variations in sample preparation. In this regard, International application WO 03/054551 is exemplary, and is specifically incorporated in the present invention.

Each spot of the array may comprise a mixture of polynucleotides of different sequences. These mixtures may comprise degenerate polynucleotides of the structure NxByNz, wherein N represents any of the four bases and varies for the polynucleotides in a given mixture, B represents any of the four bases but is the same for each of the polynucleotides in a given mixture, and x, y, z are integers. Alternatively, spots may comprise mixtures of polynucleotides that correspond to different regions of a known nucleic acid; these regions may be overlapping, adjacent, or non-adjacent. Arrays comprising these types of mixtures are useful in, for example, identifying specific nucleic acids, including those from particular pathogens or other organisms. Both types of mixtures are discussed in WO 98/31837.

A predefined region or spot may have any convenient shape, e.g., circular, rectangular, elliptical, wedge-shaped, etc. A predefined region as determined from the planar, two dimensional (2D) top surface of the substrate may be smaller than about 1 cm$^2$ or less than 1 mm$^2$. Usually, the regions have an area of less than 50,000 µm$^2$, more usually less than 10,000 µm$^2$ and may be less than 100 µm$^2$ or may be less than 10 µm$^2$.

The predefined regions on the substrate are spatially arranged and laid out in precise patterns, such as rows of dots, or rows of squares, or lines to form distinct arrays. The term "microarray" as used in the present specification refers to a porous substrate, with a matrix of target-molecules arrayed at specific positions.

The substrate surface which may have immobilized target molecules thereon (external and/or internal surface) is also referred to as active surface. Target molecule immobilization may be direct or by synthesis. Immobilization of presynthesdized polynucleotides at different spatial addresses yields an array of polynucleotides whose sequences are identifiable by their spatial addresses. In cases involving in situ synthesis of polynucleotides, the polynucleotides are synthesized in their usual manner. The synthetic scheme yields an array of polynucleotides whose sequences are identifiable by their spatial addresses.

The term "target molecule" as used in this specification refers to a molecule capable of binding to an analyte molecule. A target molecule may be directly bound to the substrate or via a substrate binding substance such as an activating group and/or a linker.

The present invention relates to microarray analysis of samples to identify and quantify analyte molecules such as nucleic acid sequences. Typical assays based upon the formation of specific target/analyte binding pairs or hybrids include a reporter system which provides a detectable signal indicative of the formation of a specific binding pair. Said reporter system may be a label which can comprise a fluorescent material, a radioactive material, any other signalling moiety, or a material which is further reactive with another species to form a colored complex or some other such detectable reaction product.

Accordingly, in one embodiment, a method as described herein is provided wherein said reporter system is capable of inducing a colour reaction and/or capable of bio-, chemi- or photoluminescence.

In a further embodiment, a method as described herein is provided wherein said reporter system is a fluorescence quenching system.

As well known in the art, fluorescence quenching systems are characterized by fluorophore and quencher moieties in a configuration which results in quenching of fluorescence in the intact "detection probe" which carries these moieties. An optimal signal to noise ratio is achieved if fluorophore and quencher moieties are located on the 3' and 5' termini of the probe. However, less than optimal fluorescence quenching may occur because the fluorophore and quencher moieties are separated in space and the transfer of energy is most efficient when they are close. Alternative probe designs may therefore comprise a probing sequence embedded within two complementary arm sequences; so-called molecular beacons. In the absence of an analyte sequence or analyte molecule, the arm sequences anneal to each other to thereby form a loop and hairpin stem structure which brings the fluorophore and quencher together. When contacted with an analyte nucleic acid or analyte molecule, the complementary probing sequence and analyte sequence/region will hybridize. Because the hairpin stem cannot coexist with the rigid double helix that is formed upon hybridization, the resulting conformational change forces the arm sequences apart and causes the fluorophore and quencher to be separated. When the fluorophore and quencher are separated, energy of the donor fluorophore does not transfer to the acceptor moiety and the fluorescent signal is then detectable. Since unhybridized molecular beacons are non-fluorescent, it is not necessary that any excess detection probe be removed from an assay.

The term "fluorescent donor" refers to the radical of a fluorogenic compound which can absorb energy and is capable of transferring the energy to another fluorogenic molecule or part of a compound. Suitable donor fluorogenic molecules include, but are not limited to, coumarins and related dyes, xanthene dyes such as fluoresceins, rhodols, and rhodamines, resorufins, cyanine dyes, bimanes, acridines, isoindoles, dansyl dyes, aminophthalic hydrazides such as luminol and isoluminol derivatives, aminophthalimides, aminonaphthalimides, aminobenzofurans, aminoquinolines, dicyanohydroquinones, and europium and terbium complexes and related compounds.

The term "quencher" refers to a chromophoric molecule or part of a compound which is capable of reducing the emission from a fluorescent donor when attached to the donor. Quenching may occur by any of several mechanisms including fluorescence resonance energy transfer, photo-induced electron transfer, paramagnetic enhancement of intersystem crossing, Dexter exchange coupling, and excitation coupling such as the formation of dark complexes. A quencher may operate via fluorescence resonance energy transfer. Many quenchers can re-emit the transferred energy as fluorescence. Examples include coumarins and related fluorophores, xanthenes such as fluoresceins, rhodols, and rhodamines, resorufins, cyanines, difluoroboradiazaindacenes, and phthalocyanines. Other chemical classes of quenchers generally do not re-emit the transferred energy. Examples include indigos, benzoquinones, anthraquinones, azo compounds, nitro compounds, indoanilines, di-and triphenylmethanes.

The term "dye" refers to a molecule or part of a compound that absorbs specific frequencies of light, including but not limited to ultraviolet light. The terms "dye" and "chromophore" are synonymous. The term "fluorophore" refers to a chromophore that fluoresces.

In a further embodiment, a method as described herein is provided wherein said fluorescence quenching system is a molecular beacon.

The complementary probing sequence of a molecular beacon as useful in the present invention may be a DNA, RNA or PNA (see U.S. Pat. No. 6,361,942) sequence.

As molecular beacons are susceptible to degradation by endonucleases and exonucleases, the 5' end of the oligonucleotide may be rendered impervious to nuclease digestion by including one or more modified internucleotide linkages as disclosed in e.g. U.S. Pat. No. 5,691,146. Also, as suggested in U.S. Pat. No. 5,691,146, a PNA or peptide may be used as a nuclease resistant linkage to thereby modify the 5' end of the nucleotide probe and render it impervious to nuclease digestion.

A particular useful reporter system in the methods as described herein includes labelling of the target member to provide a capture-probe-based analyte sequence detection system which may generate a detectable signal which is indicative of the presence, absence and quantity of one or more analyte sequences or analyte molecules of interest in a sample. As such, a "detection probe" as described above may be in itself a target molecule or capture probe immobilized on the substrate. As such, the present invention contemplates that target molecules used herein, may be molecular beacons.

Accordingly, a method as described herein is provided, wherein said reporter system is integrated within said target molecule.

The mode of detection will depend on the nature of the label. For fluorescent labels, the background signals can be conveniently quantified by scanning the array with a confocal camera or with a CCD camera, as is well known in the art.

Samples are generally manipulated in order to isolate and/or characterize the analyte. In many instances, analyte species will be present in the sample at very low concentrations; hence, the detectable signal produced thereby will be very weak. Analyte amplification techniques, such as polymerase chain reaction (PCR) amplification may be applied to a sample containing nucleic acids or nucleic matter so as to increase the concentration thereof. Analyte nucleic acids may also be processed and converted to other nucleic acids using technology known in the art such as reverse transcription, e.g. mRNA, cDNA, cRNA, and the like. The analyte nucleic acids may be isolated from a tissue or cell of interest using any method known in the art. Total RNA or its transcriptionally active fraction mRNA can be isolated from a tissue and labelled and used directly as analyte nucleic acid, or it may be converted to a labelled cDNA, cRNA, etc. via methods such as reverse transcription, transcription, Tyras, NASBA and/or PCR. Generally, such methods will employ the use of oligonucleotide primers, and the primers can be anchored by a bacteriophage RNA polymerase promoter. The primers may be designed to copy a large spectrum of RNA species, e.g. oligo-dT primers or random hexamers, or designed specifically to copy a subset of genes of interest. After the copying step, i.e. conversion of mRNA to cDNA, cDNA can be amplified by PCR or by linear amplification using bacteriophage RNA polymerase mediated transcription, NASBA or Tyras. The analyte nucleic acid sequences may also be generated using a set of a representative number of gene specific amplification primers.

In the present invention methods are provided wherein sample manipulation such as e.g. amplification is integrated within the microarray analysis.

As used herein, "amplification" refers to the increase in the number of copies of a particular nucleic acid analyte of interest wherein said copies are also called "amplicons" or "amplification products".

As used herein, "amplification components" refers to the reaction reagents such as enzymes, buffers, and nucleic acids including amplification primers and nucleotides necessary to perform an amplification reaction to form amplicons or amplification products of an analyte nucleic acid of interest. An amplification primer is a nucleic acid molecule with a 3' terminus that is either "blocked" and cannot be covalently linked to additional nucleic acids or that is not blocked and possesses a chemical group at the 3' terminus that will allow extension of the nucleic acid chain such as catalyzed by a DNA polymerase or reverse transcriptase. Amplification primers as used within the present invention are typically in solution and are not immobilized on the solid microarray substrate. Therefore, the microarray assays of the present invention comprise amplification primers that are clearly distinct in composition and function from the immobilized target molecules. As such the assays of the present invention include an integrated amplification step within the chip rather than an "on-chip" amplification step.

If not integrated within the target molecule (i.e. when the target molecule in itself is not a detector probe such as e.g. a molecular beacon), the reporter system including the detection probe such as provided by a molecular beacon may be added to the mixture of amplification components. Two or more differently labelled reporter systems or fluorophore quenching probes or molecular beacons may be added to said mixture for the purpose of multiplex applications to analyse a sample for e.g. plural allelic variants (wild type and mutant(s)) by which the fluorescent colour generated during amplification demonstrates the genotype. Alternatively, different immobilized reporter systems may also carry different labels.

Useful analyte amplification strategies include the polymerase chain reaction (PCR), strand displacement amplification (SDA), and nucleic acid sequence based amplification (NASBA).

The polymerase chain reaction (PCR) is widely used and described, and involves the use of primer extension combined with thermal cycling to amplify a target sequence; see U.S. Pat. No. 4,683,195 and U.S. Pat. No. 4,683,202, and PCR Essential Data, J. W. Wiley & sons, Ed. C. R. Newton, 1995, all of which are incorporated by reference. In addition, there are a number of variations of PCR which also find use in the invention, including "quantitative competitive PCR" or "QC-PCR", "arbitrarily primed PCR" or "AP-PCR", "immuno-PCR", "Alu-PCR", "PCR single strand conformational polymorphism" or "PCR-SSCP", allelic PCR; "reverse transcriptase PCR" or "RT-PCR", "biotin capture PCR", "vectorette PCR". "panhandle PCR", and "PCR select cDNA subtraction", among others.

Strand displacement amplification (SDA) is generally described in Walker et al., in Molecular Methods for Virus Detection, Academic Press, Inc., 1995, and U.S. Pat. No. 5,455,166 and U.S. Pat. No. 5,130,238, all of which are hereby incorporated by reference.

The TYRAS amplification method as disclosed in WO 99/43850, hereby incorporated by reference, is a non-selective poly-A mRNA amplification method which does not encompass cDNA synthesis. The method comprises the hybridization of an oligonucleotide, encompassing an oligo-T stretch, to the poly-A tail of the mRNA followed by RNase H digestion opposite the oligonucleotide and extension of the newly formed 3' end of the mRNA with reverse transcriptase. In this way the T7 RNA polymerase recognition sequence (i.e. T7 promoter) that is part of the oligonucleotide encompassing an oligo-T stretch is made double stranded. Upon binding of the T7 RNA polymerase to the promoter the original mRNA molecules are transcribed in multiple RNA copies of the opposite polarity.

RNA may also be amplified according to the method as disclosed in U.S. Pat. No. 5,545,522, hereby incorporated by reference, wherein cDNA is synthesized from an RNA sequence using a complementary primer linked to an RNA polymerase promoter region complement and then antisense RNA (aRNA) is transcribed from the cDNA by introducing an RNA polymerase capable of binding to the promoter region.

Transcription mediated amplification (TMA) is an RNA transcription amplification system using two enzymes to drive the reaction: RNA polymerase and reverse transcriptase. Nucleic acid sequence based amplification (NASBA) is generally described in U.S. Pat. No. 5,409,818 and "Profiting from Gene-based Diagnostics", CTB International Publishing Inc., N.J., 1996, both of which are incorporated by reference. NASBA relies on the simultaneous activity of 3 enzymes: AMV-RT (Avian Myoblastosis Virus-Reverse Transcriptase), RNase H and T7 RNA polymerase. NASBA is a special case of the 3SR amplification reaction or self-sustained sequence replication-reaction.

The 3SR reaction is a very efficient method for isothermal amplification of target DNA or RNA sequences in vitro. This method requires three enzymatic activities: reverse transcriptase, DNA-dependent RNA polymerase and Escherichia coli ribonuclease H.

Rolling Circle Amplification (RCA), borrows some of the same molecular machinery used by viruses to rapidly churn out copies of their DNA in infected cells. In RCA, the enzyme reads around a circle of DNA—literally "rolling out" long, repeated sequences of DNA.

Accordingly, a method as described herein is provided wherein amplifying of nucleic acid molecules is by an amplification technique selected from the group comprising PCR, rtPCR, SDA, TYRAS, NASBA, RCA, 3SR, and TMA.

A particular useful microarray set-up comprises an incubator system as disclosed in International Application No. PCT/EP02102448, herewith incorporated by reference. Said incubator system comprises a chamber that is suitable for housing a substrate as described herein and a closing means to prevent contamination and hence uncontrolled reaction processes. Particular useful closing means are made of transparent material such as, but not limited to, glass or transparent plastics such as Plexiglass® and the like. Such transparent closing means is placed above the top surface of the substrate so as to allow signal detection from the top surface of said substrate.

When closed, the substrate must remain visible to enable measurement of the generated signals. Therefore a temperature control system may be provided as disclosed in International Application No. PCT/EP02/02448.

Accordingly, in one embodiment of the present invention, a method as described herein is provided, wherein a substrate is incorporated in a housing.

In a further embodiment of the present invention, a method as described herein is provided, wherein said housing comprises a closing means, said closing means placed above the top surface of the substrate.

As contemplated within the present invention, amplification components, alone or in combination with a reporter system may be provided to the substrate prior to application of the sample to the substrate. In this case, channels within the substrate may be pre-filled with amplification components and the reporter system. Alternatively, sample, reporter system and amplification components may be mixed in a sample mixture prior to application to the substrate. As a further alternative, said channels may be pre-filled with amplification components alone whereby a reporter system is immobilized within said channels thereby representing a target molecule.

Above-mentioned temperature control system may generate a suitable temperature for amplification reactions to initiate and proceed. Temperature may vary during the course of amplification (e.g. PCR). Suitable temperature variations include temperatures from 30° C. to 95° C. and 40° C. and 95° C. Also useful within the methods of the present invention is the generation of a constant temperature. Said constant temperature is generated within the array substrate as well as within the closed housing wherein said substrate may be incorporated. Therefore, upon application of the sample mixture to the substrate, amplification reactions may be initiated within the sample prior to reaching of the sample in the membrane channels. A constant temperature as useful within the present invention may be 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C. or 60° C.

In one embodiment according to the present invention, a method as described herein is provided, wherein said amplification reaction is under isothermal conditions.

An alternating flow is generated through the substrate which may be incorporated within a closed housing whereby the sample is forced to pass through the channels in said substrate from the upper side of the substrate to the lower side of the substrate and back at least one time, under conditions that are favourable to a reaction between analyte or analyte amplicons and the immobilized target molecules and/or reporter system.

Subsequent to amplification, sample analyte matter may be identified through complementary target hybridization.

In one embodiment, a method as described herein is provided wherein detecting whether binding has occurred between a target molecule and an amplified analyte nucleic acid is carried out in real-time.

As used herein, the term "analyte" or "analyte molecule", "analyte nucleic acid" and "analyte sequence" are used interchangeably. Said terms refer to a nucleic acid sequence, the presence or absence of which is desired to be detected in a sample. Analyte nucleic acid can be single-stranded or double-stranded. Additionally, the analyte nucleic acid may be nucleic acid in any form most notably DNA, RNA, PNA, including fragments thereof.

As used herein, the term "sample" refers to a substance that is being assayed for the presence of one or more analyte molecules of interest such as e.g. nucleic acids. The nucleic acid or nucleic acids of interest may be present in a mixture of other nucleic acids. A sample, containing nucleic acids of interest, may be obtained in numerous ways. Virtually any sample may be analyzed using the method according to the present specification including cell lysates, purified genomic DNA, body fluids such as from a human or animal, clinical samples, food samples, etc. Usually, the sample is a biological or a biochemical sample. The term "biological sample," as used herein, refers to a sample obtained from an organism or from components (e.g., cells) of an organism. The sample may be of any biological tissue or fluid. Frequently the sample will be a "clinical sample" which is a sample derived from a patient. Such samples include, but are not limited to, sputum, cerebrospinal fluid, blood, blood fractions such as serum including fetal serum (e.g., SFC) and plasma, blood cells (e.g., white cells), tissue or fine needle biopsy samples, urine, peritoneal fluid, and pleural fluid, or cells there from. Biological samples may also include sections of tissues such as frozen sections taken for histological purposes. The sample can be, for example, also a physiological sample.

The present invention is applicable to high-throughput genotyping of known and unknown polymorphisms and mutations. Nucleic acid mutations may be deletions and insertions, including frame-shift mutations; and base pair substitutions, including single nucleotide mutations or polymorphisms.

Accordingly, in one embodiment, the use of a method according to the present invention and as described herein is provided for identification and quantification of nucleic acids in a sample.

In a further embodiment, the use of a method according to the present invention and as described herein is provided for performing genotyping.

There are several types of DNA sequence variations in a genome. These variations include insertions, deletions and copy number differences of repeated sequences. These differences in the genetic code are called genetic polymorphisms. The most common DNA sequence variations in a genome are single base pair substitutions. These are generally referred to as single nucleotide polymorphisms (SNPS) when the variant allele has a population frequency of at least 1%. SNPs may be classified by where they appear in the genome. For example, a single nucleotide polymorphism may be classified as a coding SNP (cSNP) when it is in a region encoding a protein, or genome SNP (gSNP) when it is detected anywhere in a genome, without reference to whether it is in a coding region. Coding SNPs include silent SNPs (sSNP), and SNPs that may be in regions associated with coding sequences, such as regulatory regions or elements (e.g., regulatory SNPs, or rSNPs) and introns (e.g., intron SNPs, or iSNPs).

SNPs are particularly useful in studying the relationship between DNA sequence variations and diseases, conditions and drug responses because SNPs are stable in populations, occur frequently, and have lower mutation rates than other genome variations such as repeating sequences. In addition, methods for detecting SNPs are more amenable to being automated and used for large-scale studies than methods for detecting other, less common DNA sequence variations.

In a further embodiment, the use of a method according to the present invention and as described herein is provided for performing nucleic acid mutation detection.

It is a further object of the present invention to provide a device for identifying an analyte nucleic acid sequence in a sample comprising a porous substrate, said porous substrate comprising microchannels, said microchannels having immobilized thereon a target molecule and provided with amplification components.

As such, the present invention provides devices comprising a porous substrate having microchannels filled with pre-dispensed reagents in wet or dried formulations of the components needed for the performance of the reaction.

In one embodiment, a device according to the present invention is provided wherein said microchannels having immobilized thereon a target molecule are additionally provided with a reporter system.

In a further embodiment, a device according to the present invention is provided wherein said reporter system is integrated within said immobilized target molecule.

It is a further object of the present invention to provide a kit for identifying an analyte nucleic acid in a sample comprising nucleic acid molecules, said kit comprising a device according to the present invention.

EXAMPLES

The following examples of the invention are exemplary and should not be taken as limiting in any way.

Example 1

Target Identification Using Integrated Analysis Including NASBA Amplification and Detection Through Molecular Beacons Design of the Molecular Beacon.

The probe is labelled at one prime-end with a fluorophore and the other prime-end with a quenching molecule. Additionally, a linker is attached with a protected reactive moiety that allows coupling to the surface of a solid substrate. The nucleic acid sequence of the molecular beacons is designed in such way that it specifically hybridises to the target of interest at the temperature of isothermal amplification, being 41° C. Different molecular beacons are designed to detect a variety of targets or allelic variants.

Nucleic Acid Sequence Based Amplification

The mixture comprising all amplification reagents and the target analyte is applied on the array. Temperature is set at 41° C. allowing amplification to take place within the membrane. Pressure-driven flow-through of the sample allows amplification to occur and simultaneous binding of generated amplicons to the molecular beacons which are immobilized on the surface of the substrate.

Detection

A fluorescent signal is only generated upon binding of the target to the molecular beacon, and is proportional to the amount of target present. The fluorescence is measured in real-time using a fluorescence microscope during the amplification reaction. Sequence information on different targets present is obtained by lightening of specific spots. Target quantification is accurately performed by determining the incubation time at which the fluorescent signal of interest becomes detectable above background (threshold fluorescence level), the so-called threshold time. The lower the initial copy number in the (biological) sample, the higher the threshold time to reach the threshold fluorescence level. Relative quantification is performed by comparison of the threshold time to e.g. housekeeping genes, or using a standard curve containing known amounts of target of interest.

Example 2

Target Identification Using Integrated Analysis Including SDA Amplification and Detection Through Molecular Beacons Probe Design and Immobilization Oligonucleotide probes are designed containing the reactive moiety at the 5'-end that allows binding to the surface of a solid substrate. These oligonucleotides serve as capture probes for the target DNA. Additionally, a molecular beacon is designed as detection probe for the nucleic acid of interest, and contains a fluorophore at the 5'-end and a quencher at the 3'-end.

Amplification Using SDA.

A mixture comprising amplification reagents, primers and molecular beacons is applied to the array. The amplification reaction is performed under isothermal conditions. The combined action of a DNA polymerase and a restriction endonuclease exponentially copies a target DNA sequence onto an immobilised probe. The product of this reaction is a double stranded DNA hybrid of which one strand is anchored to the solid substrate. The unanchored strand is removed, resulting in single stranded antisense DNA (asDNA) that is immobilised to the solid substrate.

Detection

The molecular beacon hybridises to the anchored asDNA strand if it is complementary and generates a fluorescent signal, which is proportional to the amount of nucleic acid present. This enables both identification of target sequence and accurate quantification of said target sequence. In SNP-detection, two differently labeled molecular beacons may be added to the mixture, both recognizing a different allelic variant (wild-type or mutant). As a result, the fluorescent colour generated during amplification demonstrates the genotype.

The invention claimed is:

1. A method for identifying an analyte nucleic acid in a sample comprising the steps of:
   (a) providing a solid porous substrate, said substrate comprising a plurality of micro-channels, wherein said micro-channels have immobilized thereon a target molecule capable of binding to an analyte present in said sample; wherein said channels are further provided with
      analyte amplification components,
      a reporter system, and
      said sample;
   (b) amplifying analyte nucleic acid molecules present within said sample; and
   (c) allowing binding to take place between an amplified analyte nucleic acid obtained in step (b), said target molecule immobilized onto the channels of said substrate, and said reporter system, wherein said reporter system allows detecting whether binding has occurred between said target molecule and said analyte nucleic acid.

2. The method according to claim 1, wherein said reporter system is integrated within said target molecule.

3. The method according to claim 1 or 2, wherein said reporter system is capable of inducing a colour reaction and/or capable of bio-, chemi- or photoluminescence.

4. The method according to claim 3, wherein said reporter system is a fluorescence quenching system.

5. The method according to claim 4, wherein said fluorescence quenching system is a molecular beacon.

6. The method according to claim 1, wherein said detecting whether binding has occurred between said target molecule and said analyte nucleic acid in step (c) is carried out in real-time.

7. The method according to claim 1, wherein said amplification reaction is under isothermal conditions.

8. The method according to claim 1, wherein said amplifying of said nucleic acid molecules in step (b) is by an amplification technique selected from the group comprising PCR, SDA, TYRAS, NASBA, RCA, 3SR, and TMA.

9. The method according to claim 1, wherein said solid porous substrate is a flow-through substrate.

10. The method according to claims 1, wherein said solid porous substrate is a metallo oxide substrate.

11. The method according to claim 10, wherein said metallo-oxide substrate is an aluminum oxide substrate.

12. The method according to claim 1, wherein said substrate is incorporated in a housing.

13. The method according to claim 12, wherein said housing comprises a closing means, said closing means placed above the top surface of the substrate.

14. The method of claim 1, which further comprises quantifying the analyte nucleic acid.

15. The method of claim 1, which further comprises using the identified analyte nucleic acid for performing genotyping.

16. The method of claim 1, which further comprises using the identified analyte nucleic acid for performing nucleic acid mutation detection.

17. A device for identifying an analyte nucleic acid sequence in a sample comprising a porous substrate, said porous substrate comprising microchannels, said microchannels having immobilized thereon a target molecule and provided with amplification components for amplifying analyte nucleic acid molecules.

18. The device according to claim 17, wherein said microchannels having immobilized thereon a target molecule are additionally provided with a reporter system.

19. The device according to claim 18, wherein said reporter system is integrated within said immobilized target molecule.

20. A kit for identifying an analyte nucleic acid in a sample comprising nucleic acid molecules, said kit comprising a device according to any of claims 17 to 19.

* * * * *